United States Patent [19]

Lechevin

[11] 4,178,388

[45] Dec. 11, 1979

[54] NOVEL RODENTICIDAL COMPOSITIONS EMPLOYING CHLOROPHACINONE

[75] Inventor: Jean-Claude Lechevin, Lyons, France

[73] Assignee: Lipha-Lyonnaise Industrielle Pharmaceutique, Lyons, France

[21] Appl. No.: 611,908

[22] Filed: Sep. 10, 1975

Related U.S. Application Data

[63] Continuation of Ser. No. 389,114, Aug. 17, 1973, abandoned.

[30] Foreign Application Priority Data

Aug. 21, 1972 [FR] France .................................. 72.29765

[51] Int. Cl.² ................................................ A01N 9/24
[52] U.S. Cl. ........................................ 424/331; 424/84
[58] Field of Search ................................... 424/84, 331

[56] References Cited

U.S. PATENT DOCUMENTS

| | | | |
|---|---|---|---|
| 3,544,677 | 12/1970 | Lapham et al. | 424/84 |
| 3,676,545 | 7/1972 | Saggers | 424/84 |
| 3,712,943 | 1/1973 | Mayer et al. | 424/84 |

OTHER PUBLICATIONS

Chemical Abstracts, vol. 73, (1970), p. 55009x.
Chemical Abstracts, vol. 68, (1968), p. 104137v.

*Primary Examiner*—V. D. Turner
*Attorney, Agent, or Firm*—Browdy and Neimark

[57] ABSTRACT

Rodenticidal compositions in the form of solutions or emulsions are formed from an anticoagulant substance in a liquid aromatic hydrocarbon solvent in the presence of an emulsifier.

These compositions, when diluted with water, can be used for the destruction of rodents by spraying the areas in which grow vegetables serving as foodstuffs for the rodents to be destroyed.

9 Claims, No Drawings

NOVEL RODENTICIDAL COMPOSITIONS EMPLOYING CHLOROPHACINONE

This is a continuation of application Ser. No. 389,114, filed Aug. 17, 1973, now abandoned.

FIELD OF THE INVENTION

This invention relates to new rodenticidal compositions effective against small rodents such as, for example rats and mice.

BACKGROUND OF THE INVENTION

It is known that several derivatives of 1,3-indanedione, particularly those disclosed in the Applicants' French Pat. No. 1,269,638, have the property of lowering the amount of prothrombin in the blood and as a result can be used as rodenticides, because they bring about in rodents a high mortality rate due to internal haemorrhage. Such anticoagulant substances are usually mixed with a carrier which can be eaten by the rodents, for example a cereal, to form a bait. A disadvantage of such a bait is that on prolonged storage it becomes heterogeneous with the result that the rodenticidal substance accumulates towards the bottom of the bait, so that the uniform rodenticidal activity of the bait is lost.

SUMMARY OF THE INVENTION

It has now been found that, in order to destroy certain varieties of rodents, such as Pitymys Pinetorum (pine mouse), Pitymys subterraneus de Selys Longchamps (underground vole), Pitymys duodecimcostatus de Selys Longchamps (Mediterranean pine vole), Arvicola Sapidus (water vole), Arvicola Terrestus (land vole), Microtus arvalis pallas (meadow mouse), Apodemus Sylvaticus (field mouse), Fiber Zibethicus (musk rat), which live in fields, meadows, orchards, seed-beds, nurseries and the like, it is advantageous for the anticoagulant substance to be finely and uniformly sprayed over large areas wherein are growing vegetables which serve as animal feed, for the rodents to be destroyed. The spraying operation can most conveniently be carried out with liquid compositions which contain the anticoagulant substance in dissolved form or in suspension, it being possible for such compositions to be diluted with from 10 to 500 times their volume of water at the time of use. The diluted emulsions can be sprayed onto the ground by means of the spraying devices normally used in agriculture, so as to provide a regular distribution of the anticoagulant substance.

These liquid compositions have the advantage of not becoming separated into their constituents throughout the time which a spraying operation lasts, of not causing damage to the apparatus used for the spraying and of not clogging the orifices of these latter.

DETAILED DESCRIPTION OF THE INVENTION

Thus, in accordance with the present invention, there is provided a rodenticidal composition comprising a solution or emulsion of 2-($\alpha$-p-chlorophenyl-$\alpha$-phenylacetyl)-1,3-indanedione (the common name for which is "chlorophacinone") in a liquid monocyclic aromatic hydrocarbon solvent in the presence of an emulsifier.

Benzene and benzene derivatives which are substituted by one or more straight- or branched-chain saturated alkyl radicals are suitable for use as the aromatic hydrocarbon solvent in the rodenticidal composition.

It is advantageous to use, as the benzene derivative, benzene substituted by at least one methyl, ethyl, propyl, isopropyl, butyl, isobutyl, amyl, isoamyl, sec. amyl, tert. amyl or isohexyl radical.

The benzene may be substituted by several identical, or by different, alkyl radicals.

Xylene (i.e. dimethylbenzene) is a solvent which has been found to be particularly suitable. Xylene can be used in the form of a mixture of its three isomers, or in the o-xylene (1,2-dimethylbenzene), m-xylene (1,3-dimethylbenzene) or p-xylene (1,4-dimethylbenzene) form.

Toluene (i.e. methylbenzene), as well as cumene (i.e. isopropylbenzene), and cymene (i.e. isopropyl-methylbenzene) used in the form of a mixture of isomers or in the form of o-cymene (2-isopropyl-1-methylbenzene), m-cymene (3-isopropyl-1-methylbenzene), or p-cymene (4-isopropyl-1-methylbenzene) are solvents which have also been found to be most useful.

Examples of other useful solvents are amylbenzene, sec. amylbenzene, tert. amylbenzene, isoamylbenzene, butylbenzene, sec. butylbenzene, tert. butylbenzene, isobutylbenzene, ethylbenzene, diethylbenzene in the 1,2 1,3 or 1,4-positions, triethylbenzene in the 1,2,4 or 1,3,5-positions, propylbenzene, pentamethylbenzene, pentaethylbenzene, isohexylbenzene, o-propyl-toluene (1-methyl-2-propylbenzene), m-propyl-toluene (1-methyl-3-propylbenzene) and p-propyl-toluene (1-methyl-4-propylbenzene).

The chlorophacinone may be present in the composition in an amount of from 5 to 10%, preferably 6 to 8%, by weight, whilst the aromatic hydrocarbon solvent may be present in an amount of from 75 to 85%, preferably 75 to 80%, by weight.

The rodenticidal composition contains an emulsifier, which may be present in an amount of from 2 to 20% by weight, preferably about 10%. The emulsifier may be a soluble metallic sulphonate or a polyoxyethylene ether, or mixtures thereof.

If desired, the rodenticidal composition can contain dipropylene glycol in an amount of up to 5% by weight.

If further desired, the rodenticidal composition may contain a fixative adjuvant in an amount of up to 1% by weight. This adjuvant can be poly-(methylene-p-nonylphenoxy)-$\omega$-poly-(oxypropylene) or 1,3-dihydroxypropane.

When required for use, the rodenticidal composition of the invention will normally be diluted with from 10 to 500 times its volume of water to form an emulsion ready for spraying.

EXAMPLES

The following Examples illustrate the invention.

EXAMPLE 1

| Formula No. | 1 | 2 | 3 | 4 | 5 | 6 |
|---|---|---|---|---|---|---|
| Chlorophacinone | 6 | 8 | 6 | 8 | 6 | 8 |
| Dipropylene glycol | 0 | 0 | 5 | 5 | 5 | 5 |
| Emulsifier | 10 | 10 | 10 | 10 | 10 | 10 |
| Fixative adjuvant | 0 | 0 | 1 | 1 | 0 | 0 |
| Xylene | 84 | 82 | 78 | 76 | 79 | 77 |

EXAMPLE 2

| Formula No. | 7 | 8 | 9 | 10 | 11 | 12 |
| --- | --- | --- | --- | --- | --- | --- |
| Chlorophacinone | 5 | 7 | 6 | 8 | 5 | 9 |
| Dipropylene glycol | 5 | 0 | 5 | 5 | 5 | 0 |
| Emulsifier | 10 | 10 | 10 | 10 | 10 | 10 |
| Fixative adjuvant | 0 | 1 | 0 | 0 | 1 | 0 |
| Benzene | 80 | 82 | 79 | 77 | 79 | 81 |

EXAMPLE 3

| Formula No. | 13 | 14 | 15 | 16 | 17 | 18 |
| --- | --- | --- | --- | --- | --- | --- |
| Chlorophacinone | 10 | 8 | 6 | 8 | 6 | 8 |
| Dipropylene glycol | 0 | 5 | 0 | 5 | 5 | 5 |
| Emulsifier | 10 | 10 | 10 | 10 | 10 | 10 |
| Fixative adjuvant | 0 | 0 | 1 | 1 | 0 | 0 |
| Toluene | 80 | 77 | 83 | 76 | 79 | 77 |

EXAMPLE 4

| Formula No. | 19 | 20 | 21 | 22 | 23 | 24 |
| --- | --- | --- | --- | --- | --- | --- |
| Chlorophacinone | 6 | 8 | 6 | 8 | 6 | 8 |
| Dipropylene glycol | 0 | 0 | 5 | 5 | 5 | 5 |
| Emulsifier | 10 | 10 | 10 | 10 | 10 | 10 |
| Fixative adjuvant | 0 | 0 | 1 | 1 | 0 | 0 |
| Cumene | 84 | 0 | 0 | 76 | 0 | 77 |
| Cymene | 0 | 82 | 78 | 0 | 79 | 0 |

EXAMPLE 5

| Formula No. | 25 | 26 | 27 | 28 | 29 | 30 |
| --- | --- | --- | --- | --- | --- | --- |
| Chlorophacinone | 6 | 8 | 6 | 8 | 6 | 8 |
| Dipropylene glycol | 0 | 0 | 5 | 5 | 5 | 5 |
| Emulsifier | 10 | 10 | 10 | 10 | 10 | 10 |
| Fixative adjuvant | 0 | 0 | 1 | 1 | 0 | 0 |
| Amylbenzene | 84 | — | — | — | — | — |
| Butylbenzene | — | 82 | — | — | — | — |
| Ethylbenzene | — | — | — | 76 | — | — |
| 1,2-Diethyl-benzene | — | — | 78 | — | — | — |
| Triethyl-benzene | — | — | — | — | — | 77 |
| Propyl-benzene | — | — | — | — | 79 | — |

EXAMPLE 6

The rodenticidal activity of the compositions of the invention was verified in the following manner: 1 kg. of wheat grains was spread over a flat surface of 1 square meter in a single layer, so that all the grains were in contact with the surface. A quantity of the rodenticidal composition was diluted with water to obtain 100 ml. of an aqueous emulsion containing 0.050 g. of chlorophacinone. This aqueous emulsion was sprayed uniformly over the surface of the grains.

The sprayed grains were given for consumption by rats placed under the test conditions of the protocol defined at the International Conference in London in October 1958 concerned with destruction of rodents considered as vermin. The rodenticidal activity is the ratio between dead rats after 8 days and the number of rats used in the test.

| Formula No. | Mortality | Formula No. | Mortality |
| --- | --- | --- | --- |
| 1 | 9/10 | 16 | 9/10 |
| 2 | 9/10 | 17 | 10/10 |
| 3 | 10/10 | 18 | 10/10 |
| 4 | 10/10 | 19 | 9/10 |
| 5 | 8/10 | 20 | 8/10 |
| 6 | 9/10 | 21 | 8/10 |
| 7 | 10/10 | 22 | 9/10 |
| 8 | 9/10 | 23 | 10/10 |
| 9 | 9/10 | 24 | 9/10 |
| 10 | 8/10 | 25 | 10/10 |
| 11 | 8/10 | 26 | 9/10 |
| 12 | 9/10 | 27 | 8/10 |
| 13 | 10/10 | 28 | 10/10 |
| 14 | 9/10 | 29 | 9/10 |
| 15 | 8/10 | 30 | 10/10 |

I claim:

1. A rodenticidal composition for use as a spray when diluted with water, comprising a solution of 2-($\alpha$-p-chlorophenyl-$\alpha$-phenylacetyl)-1,3-indanedione in an amount of from 5–10% by weight, in a liquid monocyclic aromatic hydrocarbon solvent which is benzene or benzene substituted by at least one straight-chain or branched-chain saturated alkyl radical selected from the group consisting of methyl, ethyl, propyl, isopropyl, butyl, isobutyl, sec. butyl, tert. butyl, amyl, isoamyl, sec. amyl, tert. amyl and isohexyl, the said liquid solvent being present in an amount of from 75–85% by weight, in the presence of an emulsifier in an amount of from 2–20% by weight.

2. A rodenticidal composition in accordance with claim 1 wherein said emulsifier is selected from the group consisting of soluble metallic sulphonic emulsifiers, polyoxyethylene ether emulsifiers and mixtures thereof.

3. A rodenticidal composition as claimed in claim 2, and further comprising dipropylene glycol in an amount of up to 5% by weight.

4. A rodenticidal composition as claimed in claim 3, and further comprising a fixative adjuvant in an amount of up to 1% by weight, the said fixative adjuvant being poly-methylene-p-nonylphenoxy-$\omega$-poly(oxypropylene) or 1,3-dihydroxypropane.

5. A rodenticidal composition as claimed in claim 1, wherein said liquid monocyclic aromatic hydrocarbon solvent is a benzene derivative substituted by at least two identical ones of said alkyl radicals.

6. A rodenticidal composition as claimed in claim 1, wherein said liquid monocyclic aromatic hydrocarbon solvent is a benzene derivative substituted by at least two different ones of said alkyl radicals.

7. A rodenticidal spray composition comprising a composition as claimed in claim 1, diluted with from 10 to 500 times its volume of water.

8. A method of destroying small rodents which comprises spraying a rodenticidal spray composition as claimed in claim 7 over an area in which are growing vegetables which serve as animal feed for the rodents to be destroyed.

9. A method according to claim 8, wherein the rodents to be destroyed are selected from the group consisting of pine mouse, underground vole, Mediteranean pine vole, water vole, land vole, meadow mouse, field mouse and musk rat.

* * * * *